United States Patent [19]

Bartlett et al.

[11] Patent Number: 5,317,086
[45] Date of Patent: May 31, 1994

[54] CYSTEINE PROTEINASE INHIBITORS AND INHIBITOR PRECURSORS

[75] Inventors: Paul A. Bartlett, Kensington; Mary M. Mader, El Cerrito, both of Calif.

[73] Assignee: The Regents of the University of California, Oakland, Calif.

[21] Appl. No.: 848,377

[22] Filed: Mar. 9, 1992

[51] Int. Cl.$^5$ .................. C07K 5/00; C07K 7/00; A61K 37/00
[52] U.S. Cl. .................. 530/327; 530/331; 530/330; 530/329; 530/328
[58] Field of Search .................. 514/19, 18, 17, 16, 514/15, 14; 530/331, 330, 329, 328, 327

[56] References Cited

U.S. PATENT DOCUMENTS 4,883,863 11/1989 Abe et al.
5,055,451 10/1991 Krantz et al.

OTHER PUBLICATIONS

Krantz et al., "Peptidyl (Acyloxy)methyl Ketones and the Quiescent Affinity Label Concept", Biochemistry, 30, 4678–4687 (1991).
Rich, "Inhibitors of Cysteine Proteinases", Chpt. 4 in Proteinase Inhibitors, Elsevier Science Publishers (1986).
Shaw et al., "The Specificity of Cathepsin B", Acta Biol. Med. Germ., 40, 1503–1511 (1981).
Smith et al., "Inhibition of Cathepsin B by Peptidyl Aldehydes and Ketones: Slow-Binding Behavior of a Trifluoromethyl Ketone," Biochemistry, 27, 6568–6573 (1988).
MacKenzie et al., "$^{13}$C NMR Study of the Stereospecificity of the Thiohemiacetals Formed on Inhibition of Papain by Specific Enantiomeric Aldehydes", Biochemistry, 25, 2293–2298 (1980).
Westerick et al., "Aldehydes as Inhibitors of Papain," J. of Biol. Chem., 247 (24), 8195–8197 (1972).
Shaw, "Cysteinyl Proteinases and Their Selective Inactivation," Adv. Enzymol. Relat. Areas Mol. Biol., 63, 271–347 (1990).

Primary Examiner—Lester L. Lee
Assistant Examiner—Carol A. Salata
Attorney, Agent, or Firm—Majestic, Parsons, Siebert & Hsue

[57] ABSTRACT

Compounds are provided that are useful in inhibiting cysteine or serine proteinases. The compounds define a peptide backbone with a sulfur atom substituted in the backbone. A leaving group is associated, or bonded, to a carbon atom adjacent to the sulfur atom. The leaving group is displaceable either by hydrolysis under physiological conditions (with the hydrolyzed compound forming an aldehyde enzyme inhibitor) or by an active-site nucleophile of a cysteine or serine proteinase. When the leaving group is displaced by hydrolysis, then the compound functions as a protected derivative of the aldehyde functional group and is stabilized against oxidation or degradation, yet allows for release of the aldehyde moiety at the pharmacological site of action. The peptide sulfide analogues bearing a leaving group displaced by the active-site nucleophile covalently bond cysteine or serine proteinases and thus irreversibly inhibit these enzymes.

1 Claim, 1 Drawing Sheet

CYSTEINE PROTEINASE INHIBITORS AND INHIBITOR PRECURSORS

This invention was made with government support under Grant No. R01-GM-46627, awarded by the National Institutes of Health. The government has certain rights in this invention.

FIELD OF THE INVENTION

The present invention generally relates to inhibitors of cysteine proteinases, and more particularly to stable and selective inhibitors of cysteine proteinases, either directly functioning as inhibitors or being inhibitor precursors, which incorporate sulfur as part of the peptide backbone and have a leaving group on the carbon adjacent to the sulfur.

BACKGROUND OF THE INVENTION

Cysteine proteinases contain a catalytically active cysteine sulfhydryl group and a histidine imidazole group within the active site of the enzyme. The imidazole group polarizes and deprotonates the Cysteine sulfhydryl group. Cysteine proteinases show unusual reactivity toward electrophiles relative to the nucleophilicity of sulfur in cysteine, although each cysteine proteinase appears to hydrolyze different proteins and peptide substrates at different rates. Among the members of this enzyme class are papain, cathepsin B, cathepsin H, cathepsin L, and hepatitis A viral protease. Selective inhibitors of the cysteine proteinase cathepsin B have potential therapeutic value in disease states such as proteinuria in glomerular disease, osteoclastic bone resorption, tumor metastasis, tissue damage in myocardial infarction and muscle wasting in Duchenne muscular dystrophy. The cathepsins are implicated in tumor invasion also.

Unlike the aspartic and zinc proteases, the cysteine proteases do not catalyze the direct addition of water to the amide carbonyl group, but rather the acyl moiety is transferred first to the active site thiol (e.g. Cys-25 in papain), and the thioester is cleaved in a second step. Two tetrahedral intermediates are thereby involved, both of which are covalently linked to the enzyme.

A variety of low molecular weight inhibitors of cysteine proteinases known as of 1984 selectively to inhibit such enzymes are described by Rich, *Proteinase Inhibitors* (Chapter 4, "Inhibitors of Cysteine Proteinases"), Elsevier Science Publishers (1986). One group of cysteine proteinase inhibitors are peptide aldehydes. The peptidyl aldehydes combine with the cysteine thiol to form a thiohemiacetal in the active site. These aldehyde inhibitors are generally analogs of the transition-state. However, inhibitors of the aldehyde class are not very stable in vivo (degrade very quickly) and are also not very shelf-life stable. Although other classes of inhibitors are known (such as peptidyl chloromethanes and peptidyl diazomethanes), these have varying degrees of affinity for selectivity and often have some non-specific activity that raises potential problems of side effects.

Krantz et al., *Biochemistry*, 30, pp. 4678–4687 (1991) and Krantz et al., U.S. Pat. No. 5,055,451, issued Oct. 8, 1991, describe aryloxy and arylacyloxy methyl ketones as thiol protease inhibitors, and particularly certain inhibitors of Cathepsin B. Shaw, *Adv. Enzymol. Relat. Areas Mol. Biol.*, 63, 271 (990) describes peptidyl methyl ketones with a leaving group that can contain —CHS(CH$_3$)$_2$ in designing inactivators of cysteine proteinases. However, the Shaw sulfur moieties are part of the leaving groups themselves.

SUMMARY OF THE INVENTION

In one aspect of the present invention, a compound having cysteine proteinase inhibitory action or a precursor of a cysteine proteinase inhibitor is provided having the structure

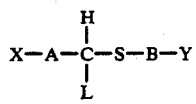

where S is part of a peptide isostere backbone, A and B are each one or more peptide residues, which can also include substituents such as an alkyl, a cycloalkyl, a cycloalkylalkyl, a phenyl, a phenylalkyl, or an alkoxy in what would otherwise be part of a peptide backbone of the peptide residue(s), X and Y are each either hydrogen, hydroxy, or a peptide protecting group, and L is a leaving group. In a first embodiment of the invention, L is preferably a non-hindered ester, while with a second embodiment of the invention L is preferably a halogen, a phosphate ester, or a hindered carboxylate ester. The first embodiment can be used as a cysteine protease inhibitor precursor, while the second embodiment can be used directly as a cysteine proteinase inhibitor. With both embodiments, the sulfur atom activates the leaving group.

IN THE DRAWING

FIG. 1 illustrates the inhibition occurring with papain in the presence of an inventive inhibitor embodiment.

DETAILED DESCRIPTION OF THE PREFERRED EMBODIMENTS

Figure 1:
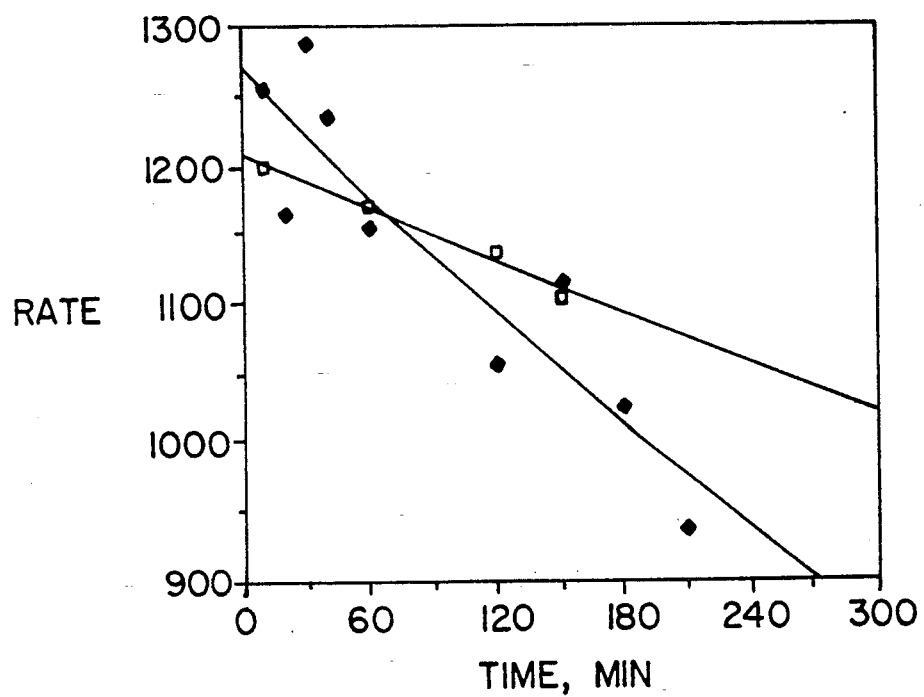

Compounds of this invention have the general structure illustrated by Formula 1.

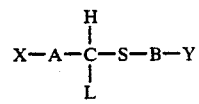

FORMULA 1

There are two preferred embodiments of this invention, which differ in the nature of L. Both embodiments are inhibitors of cysteine proteinases, and both embodiments have the L leaving group on the carbon adjacent to a sulfur atom. In both embodiments, L is a leaving group that is displaceable when the Formula 1 compound is administered, such as in a therapeutic method. However, in a first embodiment the leaving group is displaced by slow hydrolysis under aqueous (preferably physiologic) conditions. Particularly preferred leaving groups for the first embodiment are non-hindered esters. With a second embodiment of the invention, the leaving group is resistant to hydrolysis, but is reactive towards nucleophiles, such as the active-site nucleophile represented by cysteine and serine peptidases. Preferred leaving groups of the second embodiment are halogens, phosphate esters and hindered carboxylate esters. The leaving groups and applications for the two embodiments of the invention will be more fully described hereinafter.

In the Formula 1 structure of the invention, X is hydrogen or a peptide amino-end blocking group. Y is hydroxy or a peptide carboxyl-end blocking group. X preferably is a peptide amino-end blocking group and Y preferably is a peptide carboxyl-end blocking group. One of A and B is a peptide residue, and the other is a bond or a peptide residue, or an isosteric form thereof, which can also include non-amino acid moieties as will be further described.

By "peptide amino-end blocking group" is meant, for example, an alkoxy-ω-oxoalkanoyl of 2-10 carbon atoms, alkoxycarbonyl of overall 2 to 10 carbon atoms, alkanoyl of overall 2 to 10 carbon atoms, cycloalkylcarbonyl of overall 4 to 8 carbon atoms, carbamoyl, alkylcarbamoyl, or dialkyl carbamoyl, a benzoyl, an alkylsulfonyl of overall 1 to 10 carbon atoms, especially alkoxycarbonyl of overall 4 to 8 carbon atoms, particularly tert-butoxycarbonyl (BOC), or alkanoyl of overall 2 to 6 carbon atoms, particularly isovaleroyl (Iva). Cycloalkylcarbonyl preferably is of overall 4, 6 or 7 carbon atoms. Alkylsulfonyl preferably is of 3 to 6 carbon atoms, and preferably is branched.

By "peptide carboxyl-end blocking group" is meant, for example, alkoxy of to 5 carbon atoms, amino, alkylamino of 1 to 5 carbon atoms, dialkylamino of independently 1 to 5 carbon atoms in the alkyl moieties thereof, (1-benzylpiperidin-4-yl)-amino or (pyridin-2-yl)methylamino, in particular alkoxy of 1 to 5 carbon atoms, amino, alkylamino of 1 to 5 carbon atoms, (1-benzylpiperidin-4-yl)amino or (pyridin-2-yl)methylamino, especially alkoxy of 1 to 3 carbon atoms, in particular methoxy or ethoxy.

By use of the term "peptide residue" for A and B is meant to include one or more amino acids. When there is more than one amino acid residue in a peptide residue, then they are normally linked by a peptidic carbamoyl group, i.e. by —CONH—. Preferably a peptide residue consists of natural amino acid residues, but the unusual amino acid residues can also be used. When there are amino acid residues in the unnatural configuration, then there preferably are only one or two such amino acid residues, especially only one, in the unnatural configuration. "Amino acid residue" as used herein also includes imino acid residues, such as proline and hydroxyproline. A peptide residue preferably is of 1 to 7 amino acid residues, since smaller inhibitors are usually desired (at least for therapeutic applications).

It should be understood that although "X-A" of Formula 1 would normally be considered the amino terminus, and "B-Y" of Formula 1 would normally be considered the carboxyl terminus, these can be reversed. Further, the peptide residues of A and B can include non-amino acid substituents, for example in order to prevent or retard in vivo degradations. Such non-amino acid substituents will normally include an alkyl, a cycloalkyl, a cycloalkylalkyl, an aryl, an aralkyl, an alkoxy, a heteroaryl, or a heteroarylalkyl. In such an instance, alkyl preferably is of 1 to 5 carbon atoms, preferably branched, particularly isobutyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkylene moieties thereof. Aryl preferably is phenyl. Aralkyl preferably is phenylalkyl of 7 to 12 carbon atoms particularly benzyl. Alkoxy preferably is of 1 to 5 carbon atoms, preferably methoxy. Acyloxy preferably is of 2 to 6 carbon atoms, preferably acetoxy. Heteroaryl preferably is pyridinyl, especially 4-pyridinyl, thienyl, especially 2-thienyl, or furyl, especially 2-furyl, preferably pyridinyl. Heteroarylalkyl preferably has 1 to 6 carbon atoms, especially 1 carbon atom in the alkylene moiety thereof. The heteroaryl moiety of heteroarylalkyl preferably has the significances indicated above as preferred for heteroaryl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, hydroxy or amino, particularly one hydroxy, amino, chlorine or bromine, optionally in protected form where appropriate.

Inhibitors of the invention, when used as drugs for administration to mammals, are preferably in a water soluble form, such as being present as pharmaceutically acceptable salts, which is meant to include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

When the compounds of the present invention are used as drugs, they are formulated into suitable preparations according to conventional pharmaceutical procedures and generally administered by intravenous injection, intramuscular injection, intravenous infusion, oral administration, etc. A suitable dose of said compound is in the range of about 1 to 1000 mg per day per recipient.

First Embodiment

Because first embodiment compounds of the invention have a leaving group that is susceptible to hydrolysis, preferably at physiological conditions, with particularly preferred leaving groups being non-hindered esters, first embodiment compounds are inhibitor precursors which, when hydrolyzed, release the actual inhibitor in an aldehyde form. This is illustrated by Scheme 1.

Scheme 1

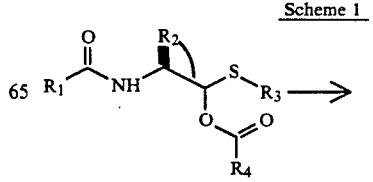

-continued
Scheme 1

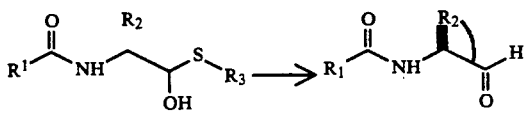

where $R_1$ is an alkyl, alkoxy, or peptidyl (and represents the X-A moieties of Formula 1), $R_2$ is an alkyl, aralkyl or peptide side chain, $R_3$ is an alkyl, aryl, aralkyl, peptidyl (and represents the Y-B moieties of Formula 1), and $R_4$ is an alkyl, aryl, amino, alkyl-amino, dialkylamino, or alkoxy (and is part of the leaving group). Thus, the hemimercaptal ester moiety of a first embodiment compound as illustrated by Scheme 1 hydrolyses slowly under aqueous conditions to release an aldehyde derivative inhibitor. The compound therefore represents a protected, or latent form, of the aldehyde inhibitor but with better pharmacodynamic properties. Generally, first embodiment compounds, or precursors, can be converted to their mercaptal esters by reaction with a thiol and an esterifying agent, such as is illustrated by Scheme 2.

Scheme 2

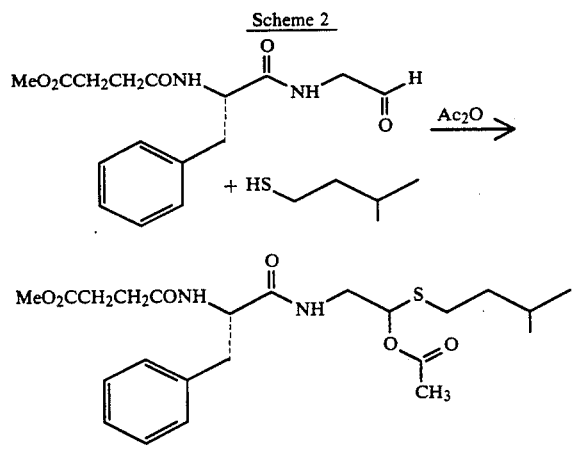

Other methods of synthesis are, however, available and possible.

By non-hindered esters for the leaving group is meant esters of formula $O_2CR$ where R is hydrogen, $CH_2R'$ where R' is an alkyl of 1 to 6 carbon atoms, cycloalkyl, aryl, and so forth.

Because pharmacologically active aldehydes can be derivatized to yield hemiacetal esters and hemimercatyl esters in accordance with this invention, the ultimate aldehyde inhibitors are thereby stabilized against oxidation or degradation and their absorption is facilitated, while allowing for slow-release (or also enzyme-catalyzed release) of the aldehyde moiety at the pharmacological site of action. By varying the thiol and the ester groups (that is, $R_3$ and $R_4$ illustrated by Scheme 1, above), the stability and pharmacodynamic properties of first embodiment precursors of the invention can be altered as desired.

Second Embodiment

A particularly preferred group of second embodiment compounds are peptide-sulfide analogs that can bond covalently to peptidases and thus inhibit these enzymes. With few exceptions, other inhibitors that bind irreversibly to peptidases are unable to take advantage of the binding affinity and specificity of the complete peptide substrate. That is, prior inhibitors have been constructed to mimic the N-terminal or the C-terminal half of the substrate, but not both. However, by appropriate choice of peptide residues and of the sulfur substituent in second embodiment compounds, our peptide-sulfides can mimic both ends of a substrate.

Most electrophilic reagents suffer from nonselective reaction with other nucleophiles (typically amino groups) in the biological system. This leads to concerns over antigenicity and toxicity. But with second embodiment compounds of the invention, the chemical nature of the peptide-sulfide acylating agent can be chosen to be such that reaction with amine nucleophiles will result in an unstable adduct that will decompose to the thiol and the peptide aldehyde and release the nucleophile. Scheme 3 illustrates the reaction of an active-site nucleophile by displacing the leaving group of a second embodiment compound and the resultant covalent bonding of the inhibitor to the enzyme.

Scheme 3

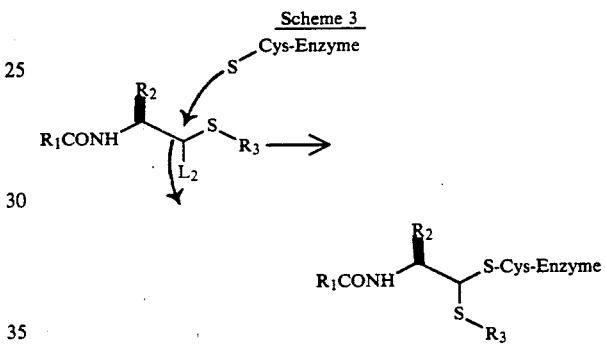

(where $L_2$ is a second embodiment leaving group).

The second embodiment leaving groups include halogens (particularly preferred being fluorine), a phosphate ester (e.g. $OPO_3R_2$ where R is hydrogen, alkyl, cycloalkyl, aryl, or aralkyl), and hindered carboxylate esters (e.g. $O_2CR$ where R is aryl, a 1-6 carbon alkyl, other branched alkyl or cycloalkyl, amino, alkylamino, or dialkylamino).

Both embodiments of the invention will be illustrated by reference to a specific one compound having the structure illustrated by Formula 2.

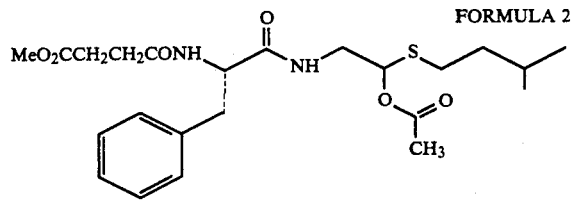

FORMULA 2

The specific inventive Formula 2 compound hydrolyzes with a half-life of about one hour at pH 7 and forms the aldehyde derivative when the —OAc leaving group is displaced. The aldehyde is a potent inhibitor of the cysteine protease papain. However, the Formula 2 compound also illustrates the second embodiment of the invention because we believe the acetate is first displaced by attack of the active site cysteine thiolate to give a mixed thiol ketone, which is bound irreversibly to the enzyme. The corresponding fluorosulfide (where L=F) inhibitors are believed particularly useful as irreversible inhibitors of the inention.

EXPERIMENTAL

General Procedures

Unless otherwise specified, all reactions were run in glassware that was previously oven dried and cooled in a dessicator, and the reaction flasks were flushed with $N_2$. Solutions of reagents were added by syringe. Organic phases obtained in extractive workups were dried by treatment with $MgSO_4$ and filtered prior to concentration by rotary evaporation.

Reagents: All commercially available amino acids and derivatives were used as obtained. Solvents were prepared as follows: amines (triethylamine ($Et_3N$), diisopropylamine ($iPr_2NH$), and pyridine) were distilled from $CaH_2$ under $N_2$ and were stored over $CaH_2$ under $N_2$. N-Methylmorpholine (NMM) was distilled from sodium and stored under $N_2$. Isobutylchloroformate was distilled immediately prior to use. Methylene chloride was distilled from $CaH_2$ under $N_2$; tetrahydrofuran (THF), diethylether ($Et_2O$) and benzene were distilled under $N_2$ from blue Na-benzophenone ketyl solutions. Acetic anhydride ($Ac_2O$) was distilled under $N_2$ from $P_2O_5$.

Instrumentation: Infrared (IR) spectra were obtained on a Perkin Elmer 1420. Melting points were obtained with a Buchi Schmelzpunktbestimmung-apparat and are uncorrected. $^1H$ NMR spectra were obtained on an instrument constructed by R. Nunlist at the Department of Chemistry, University of California, Berkeley operating at 250 MHz or a Bruker AMX at 400 MHz; $^{13}C$ spectra were obtained on the AMX at 100 MHz. Shifts are recorded in ppm and were obtained in and referenced to $CDCl_3$ at d 7.24 ppm for $^1H$ NMR and d 77.00 ppm for $^{13}C$ NMR unless otherwise noted. $^1H$ NMR coupling constants (J) are reported in Hertz (Hz). Multiplicities are indicated as follows: s=singlet, d=doublet, t=triplet, q=quartet, m=multiplet. Mass spectral analyses were obtained on an Atlas MS-12, Consolidated 12-110B or a Kratos M550 spectrometer.

Fluorescence assays of papain were conducted on a Photon Technology International Alphascan fluorimeter. A Brinkmann RM20 Lauda water bath was used to maintain solutions and the cell compartment of the fluorimeter at constant temperature. All buffer solutions were prepared with doubly distilled $H_2O$ and filtered through Millipore 0.45-mm filters.

Assays

Papain (Sigma, 2x recrystallized) (1 mg/mL) was activated at 25° C. for 30 min prior to use in a solution of 0.1mM EDTA, 0.5 mM L-cysteine hydrochloride, and 0.06 mM mercaptoethanol, and was then diluted (20 μL to 1.0 mL) and stored at 4° C. for use in the assays. The cysteine and mercaptoethanol buffers were prepared fresh daily. The standard assay conditions consisted of 50 mM phosphate, 0.2 M NaCl, 5 mM EDTA, 2 mM dithiothreitol (DTT), 0.2% bovine serum albumin (BSA) and 20% $CH_3CN$, pH 6.5. However, these concentrations were obtained by dilution of a buffer of 100 mM phosphate, 0.4 M NaCl, 10 mM EDTA, 4 mM DTT at pH 6.5 to a final volume of 1 mL with the necessary amounts of $CH_3CN$ and $H_2O$. The DTT and BSA were added fresh daily to the phosphate buffer. Kinetic measurements were performed by monitoring the fluorescence of 7-amino-4-methylcoumarin (MCA) [1 (excitation) 350 nm, 1 (emission) 460 nm] released upon hydrolysis of the substrate, CbzPheArgMCA. Assays were conducted by charging a quartz cuvette with the appropriate amount of substrate solution, variable inhibitor in $CH_3CN$, and the reaction was initiated by addition of papain to the sample cuvette. The substrate fluorescence at high concentrations ($<4K_m$) resulted in quenching, and thus $K_m$ was determined at 0.15 to 0.005 mM [S]. The $K_m$ was determined in duplicate runs by fitting rate vs. [S] using the program ENZFITTER.

A peptidyl acetoxysulfide of Formula 2 was prepared (18%, 1:1 mixture of diastereomers) (shown as 10in the below reaction Scheme 4) in five steps. Routine couplings provided methoxysuccinylphenylalanylalaninol, and oxidation of this alcohol yielded the aldehyde. The crude aldehyde was treated immediately with 3-methylbutanethiol and acetic anhydride to give the desired acetoxysulfide as a 1:1 mixture of diastereomers which were separable by HPLC. These compounds were crystalline solids that were stable during prolonged storage in a freezer. Scheme 4 illustrates the generally just described preparation, the details of which now follow in Example 1. (Example 1 uses the designations "4–10" for compounds shown in Scheme 4, where the compound 10 is an inventive inhibitor embodiment also designated "Formula 2.")

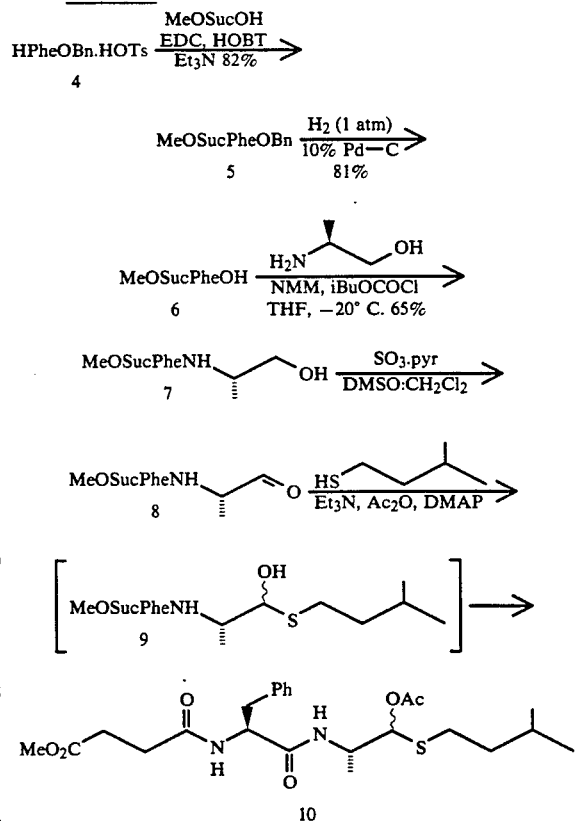

EXAMPLE 1

N-(Methoxysuccinyl)-L-phenylalanine, Benzyl Ester (5)

To a suspension of monomethyl succinate (0.6606 g, 5.00 mmol), L-phenylalanine benzyl ester, tosylate salt 4 (2.3507 g, 5.50 mmol), HOBT (0.7430 g, 5.5 mmol) and EDC (1.0514 g, 5.5 mmol) in CH$_2$Cl$_2$ (50 mL) at 25° C. was added Et$_3$N (766 μL, 5.5 mmol). The suspension cleared within 15 minutes, and the reaction mixture was allowed to stir for 19 hr at 25° C. The mixture was then diluted with CH$_2$Cl$_2$ (50 mL) and washed with 25 mL each H$_2$O, 1 N HCl, and brine. The organic phase was dried and concentrated by rotary evaporation to give the crude peptide as a thick syrup. Following flash column chromatography (40:60, EtOAc:pet. ether) the diester was obtained as a white foam (1.5254 g, 4.10 mol, 82%): mp 78°–80° C.; [a]$_D$+19.4° (c 1, CH$_2$Cl$_2$); $^1$H NMR (400 MHz, CDCl$_3$) d 7.26 (m, 10), 6.25 (d, 1, J=7.7), 5.13 (d, 1, J=12.1), 5.08 (d, 1, J=12.1), 4.90 (dd, 1, J=7.7, 5.9), 3.63 (s, 3), 3.08 (m, 2), 2.62 (t, 2, J=6.1), 2.45 (t, 2, J=6.1); $^{13}$C NMR (100 MHz, CDCl$_3$) d 173.1, 171.2, 170.9, 135.6, 134.9, 129.2, 128.5, 128.4, 126.9, 67.1, 53.1, 51.7, 37.7, 30.6, 29.0; IR (CH$_2$Cl$_2$) 3420, 1740, 1675, 1600 cm$^{-1}$; MS (EI) M+H 369 observed. Anal. Calcd for C$_{21}$H$_{23}$NO$_5$: C, 68.28; H, 6.68; N, 3.79. Found: C, 67.95; H, 6.32; N, 3.53.

N-(Methoxysuccinyl)-L-phenylalanine (6)

The diester 5 (2.418 g, 7.51mmol) was dissolved in EtOAc (50 mL) and treated with 10% Pd-C (36 mg) under 1 atm H$_2$ at 25° C. TLC indicated complete conversion to the carboxylic acid after 16 hr, and the catalyst was removed by filtration through a pad of Celite. The filtrate was concentrated by rotary evaporation and the crude syrup was recrystallized from EtOAc: pet. ether to give the acid 6 as a white solid (1.699 g, 6.10 mmol, 81%): mp 72°–74° C.; [a]$_D$+33.0° (c 1.4, MeOH); $^1$H NMR (400 MHz, CDCl$_3$) d 7.25 (m, 5) 6.35 (d, 1), 4.83 (dd, 1, J=6.3, 5.5), 3.63 (s, 3), 3.18 (dd, 1, J=14.0, 5.5), 3.08 (dd, 1, J=14.0, 6.3), 2.59 (t, 2, J=6.8), 2.45 (t, 2, J=6.8); $^{13}$C NMR (100 MHz, CDCl$_3$) d 174.6, 173.4, 171.9, 135.7, 129.3, 128.6, 127.1, 53.2, 52.0, 37.2, 30.7, 29.1; IR (CH$_2$Cl$_2$) 3320, 1730, 1640 cm$^{-1}$; MS (EI) M+H 279 observed. Anal. Calcd for C$_{14}$H$_{17}$NO$_5$: C, 60.19; H, 6.14; N, 5.02. Found: C, 60.11, H, 6.03; N, 4.74.

N-(Methoxysuccinyl)-L-phenylalanyl-L-alaninol (7)

A solution of the acid 6 (0.3203 g, 1.15 mmol) in THF (11.5 mL) was cooled to 0° C. and treated with N-methylmorpholine (126 μL, 1.15 mmol) followed by freshly distilled isobutylchloroformate (149 μL, 1.15 mmol). The mixture was stirred 5 min, L-alaninol (98 μL, 1.26 mmol) was added neat by syringe, and stirred for 10 min at −20° C. The bath was removed, and the white heterogeneous mixture was stirred at 25° C. for 50 min. The reaction mixture was poured into a separatory funnel that contained EtOAc (75 mL) and washed with 2 N HCl (10 mL), satd aq NaHCO$_3$ (10 mL), and brine (7 mL). The organic phase was dried and concentrated by rotary evaporation to give a white solid (290 mg) that was purified by flash column chromatography (100% CH$_2$Cl$_2$ to 98:2, CH$_2$Cl$_2$:MeOH). The alcohol 7 was obtained as a white solid (0.2538 g, 0.75 mmol, 65%): mp 129-132° C.; [a]$_D$ −5.4° (c 1, MeOH); $^1$H NMR (250 MHz, CDCl$_3$) d 7.27 (m, 5), 6.42 (d, 2, J=7.7, —NH), 4.67 (dd, 1, J=7.2, 6.7, —CHCH$_2$Ph), 4.01 (m, 1, —CHCH$_3$), 3.67 (s, 3, —CO$_2$CH$_3$), 3.50 (dd, 1, J=11.4, 7.7), 3.37 (dd, 1, J=11.4, 6.0), 3.14 (dd, 1, J=13.7, 6.7, —CHHPh), 3.08 (dd, 1, J=13.7 7.2, —CHHPh), 2,60 (m, 4, —COCH$_2$CH$_2$CO—), 1.10 (d, 3, J=6.8, —CHCH$_3$); $^{13}$C NMR (100 MHz, CDCl$_3$) d 173.8, 171.6, 170.7, 136.6, 129.2, 128.7, 127.0, 66.0, 54.6, 51.9, 47.7, 38.1, 30.8, 29.0, 16.6; IR (CDCl$_3$) 3420, 1730, 1660, 1500 cm$^{-1}$; MS (FAB) 337 (100), 319 (22), 262 (24). Anal. Calcd. for C$_{17}$H$_{24}$N$_2$O$_5$: C, 60.10 H, 7.19; N, 8.33. Found: C, 59.87; H, 7.21; N, 8.19.

Acetoxy sulfide 10

A cooled (0° C.) solution of the alcohol 7 (0.0496 g, 0.147 mmol) and Et$_3$N (62 μL, 0.443 mmol) was dissolved in CH$_2$Cl$_2$:DMSO (1:v:v) (200 μL), and treated with SO$_3$pyr (0.0705 g, 0.443 mmol) as a solution in CH$_2$Cl$_2$:DMSO (600 μL). The bath was removed, and the clear brown mixture was stirred at 25° C. for 30 min. The reaction mixture was poured into a beaker containing 2 mL ice slush, stirred until the ice melted, and extracted with CH$_2$Cl$_2$ (4×5 mL). The combined organic phases were washed with 2×1.5 mL each: 10% citric acid, H$_2$O, and satd aq NaHCO$_3$. The organic phase was dried and concentrated by rotary evaporation, giving 0.0371 g aldehyde 8 and alcohol 7 (approx 2:1 by integration of $^1$H NMR, 0.073 mmol aldehyde, 0.037 mmol alcohol). The crude was dissolved in dry CH$_3$CN (300 μL) and treated with 3-methylbutanethiol (7 μL, 0.080 mmol) and Et$_3$N (2 μL) at 25° C. for 4 hr. The clear pale yellow mixture was cooled to 0° C. and Et$_3$N (10 μL, 0.073 mmol), Ac$_2$O (14 μL, 0.146 mmol), and DMAP (4 mg) were added. The reaction mixture was stirred overnight (19 hr), concentrated by rotary evaporation, and purified by flash column chromatography (80:20. EtOAc: pet. ether), to give the acetylated alcohol (0.0055 g, 0.014 mmol, 38%) and the acetoxy sulfide 10 (0.0062 g, 0.013 mmol, 18%) as a 1:1 mixture of diastereomers). For 1: $^1$H NMR (250 MHz, CDCl$_3$) d 7.26 (m, 10), 6.15 (m, 4, —NH's) 5.87 (d 1, —CHOAc) 5.75 (d 1, —CHOAc) 4.65 (dd, 2, 2 x —CHCH$_2$Ph) 4.33 (m, 2, 2 x —$\overline{\text{N}}$HCH(CH$_3$)CO—), 3.68 (s, $\overline{6}$, 2 x —CO$_2$CH$_3$), 3.12 (d, 4, $\overline{2}$ x —CH$_2$Ph), 2.80-2.35 (m, 12, $\overline{2}$ x —COCH$_2$CH$_2$CO— and —SCH$_2$CH$_2$—), 2.09 (s, 3, —OCO$\overline{\text{CH}}_3$), 2.05 (s, 3, —OCO$\overline{\text{CH}}_3$), 1.65 (m, 2, 2 x —CH(C$\overline{\text{H}}_3$)$_2$), 1.49 (m, 4, 2 x —SC$\overline{\text{H}}_2$CH$_2$—), 1.20 (d, 3, —$\overline{\text{N}}$HCH(CH$_3$)CO—), 1.16 (d, 3, —NHCH(C$\overline{\text{H}}_3$-)CO—), 0.90 (dd, 12, 2 x CH(CH$_3$)$_2$).

EXAMPLE 2

Results of Assays

We anticipated that the Formula 2 (acetoxysulfide embodiment) would inhibit the enzyme due simply to the affinity of the peptide backbone for the active site. Although diastereomers were separable by HPLC, the mixture of acetoxysulfide diastereomers was initially assayed as a competitive, reversible inhibitor of papain and found to have a K$_i$ =3μM. Then the inhibitor (0.020 μM, 7K$_i$) was incubated with enzyme and diluted to determine its activity as an irreversible inhibitor. Dilution of the preincubation mixture into a high concentration of substrate (CbzPheArgMCA) quenches the inactivation reaction immediately by competition of substrate with reversible bound inhibitor. If irreversible inhibition were taking place, first order deactivation of papain would be expected.

As illustrated by FIG. 1, evidence of irreversible inhibition was seen when the inhibitor was incubated with papain and diluted 3000-fold (to 7 nM) into a buffered solution of substrate, with slow but incomplete pseudo-first order deactivation of papain (25% loss of papain activity over 3.5 hr, diamond symbol in the graph). The incomplete deactivation can be attributed to the increasing amounts of aldehyde present over time, which as a reversible inhibitor protects papain against alkylation. The dilution assay also provided evidence that the inhibition measured in the reversible assay was not due to trace amounts of aldehyde contamination. A control experiment in which the aldehyde MeOSucPheGlyCHO (0.020 μM, 666K$_i$; square symbol in the graph) was incubated with papain and diluted under similar conditions (to 7 nM, 0.2 Ki) showed an 8% loss of papain activity over 2.5 hr, ruling out the possibility that the decrease in papain activity with the inhibitor was due to enzyme death. The scatter in the graph can be attributed to experimental error that occurred in the dilution of the incubation mixture.

The hydrolysis of the acetoxysulfide inhibitor to its aldehyde form was monitored by incubation of the inhibitor (2 μM) in the buffer/20% CH$_3$CN solution. Aliquots were removed and the extent of inhibition was determined by addition of substrate (100 μM) and followed by addition of enzyme. The rate of substrate hydrolysis by papain was observed to slow as the amount of aldehyde present in the incubation buffer increased over time, and the t$_{½}$ for the conversion of acetoxysulfide to aldehyde was determined to be approx. 60 min (average of duplicate runs). At micromolar concentrations of the aldehyde (Ki>3 nM), one would expect to observe this eventual complete inhibition of papain.

Assays of Competitive Inhibition

For the acetoxysulfide inhibitor, the concentration was varied from 50 μM to 0.10 μM at [S]=0.1 mM (1.3 K$_m$). For the aldehyde, the parent dimethyl acetal was hydrolyzed in 0.3% HCl for 18 hr prior to assay, and concentration of aldehyde was varied from 262 nM to 0.262 nM. Fluorescence vs time data were collected for ≦15% of the reaction, and a straight line was fitted to the linear portion of the data. The slope was representative of the velocity, V$_i$, and the ratio of V$_o$/V$_i$ vs. [I] was plotted at constant [S] (1.3 K$_m$) to solve for K$_i$ as shown by equation (1) below.

$$V_o/V = 1 + (K_m[I]/K_i(K_m+[S])) \qquad (1)$$

Assays of Irreversible Inhibition

A mixture of 0.020 μM acetoxysulfide inhibitors and papain (1 mg/mL) in the standard assay buffer was incubated at 25° C. The rate of inactivation was followed by removing 10 μL aliquots at various times and diluting sequentially into 290 μL buffer, then removing a 10 μL aliquot of this solution and diluting into 0.050 mM substrate in 990 μL buffer (net 3000-fold dilution of 1+E, final concentration of 1 was 7 nM), and determining the remaining enzyme activity. For the aldehyde control, the same initial concentration (0.020 mM), dilution, and final concentration (7 nM) were used. The remaining enzyme activity was determined by collecting fluorescence vs time data for ≦15% of the reaction, and a straight line was fitted to the linear portion of the data.

Assay of Acetoxysulfide Inhibitor Hydrolysis

A mixture of the inhibitor (2.0 μM) in buffer with 20% CH$_3$CN was maintained in the 25° C. bath, and 970 μL aliquots were removed at periodic intervals. Substrate (100 μM) and enzyme (prepared as described above under Assays) were added, and substrate hydrolysis was monitored. The remaining enzyme activity was determined by collecting fluorescence vs time data for ≦15% of the reaction, and a straight line was fitted to the linear portion of the data to give the rate of substrate hydrolysis. Rate vs. time data were plotted to determine the half life of the acetoxysulfide in solution.

It is to be understood that while the invention has been described above in conjunction with preferred specific embodiments, the description and examples are intended to illustrate and not limit the scope of the invention, which is defined by the scope of the appended claims.

It is claimed:

1. The compound as in claim 1 having the structure

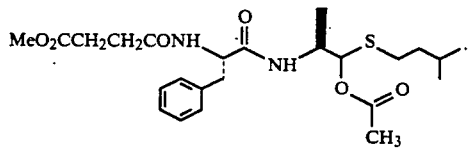

* * * * *

UNITED STATES PATENT AND TRADEMARK OFFICE
CERTIFICATE OF CORRECTION

PATENT NO. : 5,317,086

DATED : May 31, 1994

INVENTOR(S) : Bartlett et al.

It is certified that error appears in the above-identified patent and that said Letters Patent is hereby corrected as shown below:

Claim 1, Column 12, Line 38:

Replace: "The compound as in claim 1 having the structure"

With: --A compound for inhibiting cysteine or serine proteinases having the structure-- and below the chemical drawing (at about line 46), add the text:

--wherein the compound inhibits papain.--

Signed and Sealed this

Twenty-fifth Day of October, 1994

Attest:

BRUCE LEHMAN

Attesting Officer

Commissioner of Patents and Trademarks